United States Patent
Tsukernik

Patent Number: 5,868,719
Date of Patent: Feb. 9, 1999

[54] DRUG DELIVERY BALLOON CATHETER DEVICE

[75] Inventor: Vladimir Tsukernik, West Roxbury, Mass.

[73] Assignee: Boston Scientific Corporation, Natick, Mass.

[21] Appl. No.: 782,684

[22] Filed: Jan. 15, 1997

[51] Int. Cl.⁶ ................................................. A61M 5/32
[52] U.S. Cl. .................... 604/265; 604/19; 604/53; 604/96; 604/264; 604/280
[58] Field of Search .............. 604/96, 103, 264, 604/280, 19, 53, 263, 265

[56] References Cited

U.S. PATENT DOCUMENTS

| | | | |
|---|---|---|---|
| 3,699,956 | 10/1972 | Kitrilakis et al. | 128/348 |
| 4,026,296 | 5/1977 | Stoy et al. | 128/349 B |
| 4,299,226 | 11/1981 | Banka . | |
| 4,330,497 | 5/1982 | Agdanowski | 264/173 |
| 4,364,392 | 12/1982 | Strother et al. | 128/325 |
| 4,417,576 | 11/1983 | Baran | 128/207.15 |
| 4,423,725 | 1/1984 | Baran et al. | 128/207.15 |
| 4,448,195 | 5/1984 | LeVeen et al. | 128/344 |
| 4,481,323 | 11/1984 | Sterling . | |
| 4,515,593 | 5/1985 | Norton | 604/265 |
| 4,589,873 | 5/1986 | Schwartz et al. | 604/265 |
| 4,592,340 | 6/1986 | Boyles | 128/1 |

(List continued on next page.)

FOREIGN PATENT DOCUMENTS

| | | |
|---|---|---|
| 0 166 998 B1 | 1/1986 | European Pat. Off. . |
| 0 372 088 A1 | 6/1990 | European Pat. Off. . |
| 0 379 156 A2 | 7/1990 | European Pat. Off. . |
| 0 399 712 A1 | 11/1990 | European Pat. Off. . |
| 0 441 516 A2 | 8/1991 | European Pat. Off. . |
| A 380205 | 1/1924 | Germany . |
| 1196327 | 7/1965 | Germany . |
| 53-006430 | 1/1978 | Japan . |
| 54-035036 | 10/1979 | Japan . |
| 1069826 | 1/1984 | U.S.S.R. . |
| 2112646 | 7/1983 | United Kingdom . |
| WO 89/12478 | 12/1989 | WIPO . |
| WO 91/05816 | 5/1991 | WIPO . |
| WO 91/08790 | 6/1991 | WIPO . |
| WO 92/11895 | 7/1992 | WIPO . |

(List continued on next page.)

OTHER PUBLICATIONS

Chapman et al., "A Bioabsorbable Stent: Initial Experimental Results", *Circulation* (Supp III) 82:0283 (abstract) (Oct. 1990).

Deutsch et al., "Low Stress Angioplasty at 60° C.; Attenuated Arterial Barotrauma", Circulation (Supp. III) 82:0281 (abstract) (Oct. 1990).

Guyton et al., "Inhibition of Rat Arterial Smooth Muscle Cell Proliferation by Heparin: In Vivo Studies with Anticoagulant and Nonanticoagulant Heparin," *Circ. Res.* 46:625–634 (May 1980).

Ilmain et al., "Volume Transition in a Gel Driven by Hydrogen Bonding", 1991, *Nature*, 349:400–401.

Irie et al. "Stimuli–responsive polymers: chemical induced reversible phase separation of an aqueous soution of poly(N–isopropylacrylamide) with pendent crown ether groups", 1993, *Polymer*, 34(21):4531–35.

(List continued on next page.)

Primary Examiner—Wynn Wood Coggins
Assistant Examiner—N. Kent Gring
Attorney, Agent, or Firm—Fish & Richardson P.C.

[57] ABSTRACT

A medical device for delivering a drug internally to a patient's body. The medical device includes a catheter with a catheter shaft and a balloon attached to a distal end of the catheter shaft and a flexible, thin-walled sheath extending over the balloon. The sheath includes a balloon-enveloping portion having an inner diameter sized to fit closely around the balloon and a collar distal to, and having an inner diameter slightly smaller than the inner diameter of the balloon-enveloping portion. The collar terminates in an opening, and a tab extends distally from a wall of the sheath.

16 Claims, 4 Drawing Sheets

U.S. PATENT DOCUMENTS

| | | |
|---|---|---|
| 4,603,152 | 7/1986 | Laurin et al. .............................. 604/265 |
| 4,636,195 | 1/1987 | Wolinsky . |
| 4,693,243 | 9/1987 | Buras ................................. 128/207.15 |
| 4,714,460 | 12/1987 | Calderon . |
| 4,732,930 | 3/1988 | Tanaka et al. . |
| 4,769,013 | 9/1988 | Lorenz et al. ........................... 604/265 |
| 4,784,647 | 11/1988 | Gross ....................................... 604/178 |
| 4,820,270 | 4/1989 | Hardcastle et al. ........................ 604/96 |
| 4,832,688 | 5/1989 | Sagae et al. .............................. 604/101 |
| 4,876,126 | 10/1989 | Takemura et al. ...................... 428/35.7 |
| 4,909,258 | 3/1990 | Kuntz et al. ............................. 128/658 |
| 4,923,450 | 5/1990 | Maeda et al. ............................ 604/265 |
| 4,950,256 | 8/1990 | Luther et al. ............................ 604/265 |
| 4,983,166 | 1/1991 | Yamawaki ................................. 604/96 |
| 4,993,412 | 2/1991 | Murphy-Chutorian ..................... 606/7 |
| 4,994,033 | 2/1991 | Shockey et al. ......................... 604/101 |
| 5,021,044 | 6/1991 | Sharkawy ................................. 604/53 |
| 5,026,607 | 6/1991 | Kiezulas ............................... 428/423.7 |
| 5,041,100 | 8/1991 | Rowland et al. ........................ 604/265 |
| 5,047,045 | 9/1991 | Arney et al. ............................. 604/194 |
| 5,049,132 | 9/1991 | Shaffer et al. ........................... 604/101 |
| 5,087,244 | 2/1992 | Wolinsky . |
| 5,091,205 | 2/1992 | Fan ......................................... 604/265 |
| 5,102,402 | 4/1992 | Dror et al. ............................... 604/265 |
| 5,120,322 | 6/1992 | Davis et al. ............................. 604/265 |
| 5,135,516 | 8/1992 | Sahatjian et al. ........................ 604/265 |
| 5,163,906 | 11/1992 | Ahmadi ................................... 604/101 |
| 5,180,366 | 1/1993 | Woods ....................................... 604/96 |
| 5,213,576 | 5/1993 | Abiuso et al. ............................. 604/96 |
| 5,213,580 | 5/1993 | Slepian et al. ............................... 623/1 |
| 5,232,444 | 8/1993 | Just et al. .................................. 604/96 |
| 5,254,089 | 10/1993 | Wang . |
| 5,304,120 | 4/1994 | Crandell et al. .......................... 604/53 |
| 5,304,121 | 4/1994 | Sahatjian .................................. 604/53 |
| 5,328,470 | 7/1994 | Nabel et al. . |
| 5,330,467 | 7/1994 | Abela . |
| 5,336,178 | 8/1994 | Kaplan et al. . |
| 5,336,615 | 8/1994 | Bell et al. . |
| 5,370,614 | 12/1994 | Amundson et al. . |
| 5,439,446 | 8/1995 | Barry . |
| 5,462,752 | 10/1995 | Chao . |
| 5,575,815 | 11/1996 | Slepian . |
| 5,674,192 | 10/1997 | Sahatjian et al. . |
| 5,730,734 | 3/1998 | Adams et al. . |

FOREIGN PATENT DOCUMENTS

| | | |
|---|---|---|
| WO 92/11896 | 7/1992 | WIPO . |
| WO 92/13566 | 8/1992 | WIPO . |
| WO 92/15282 | 9/1992 | WIPO . |
| WO 93/11751 | 6/1993 | WIPO . |

OTHER PUBLICATIONS

Langer, "Drug Delivery," *IUPAC* Meeting, Montreal, Canada (Jul. 12, 1990).

Mamada et al., "Photoinduced Phase Transition of Gels", 1990, *Macromolecules*, 23:1517–19.

McMath et al., "Experimental Application of Bioprotective Materials to Injured Arterial Surfaces with Laser Balloon Angioplasty", *Circulation* (Supp. III) 82:0282 (abstract) (Oct. 1990).

Suzuki et al., "Phase Transition in Polymer Gels Induced by Visible Light", 1990, *Nature*, 346:345–47.

Tarcha, "Diffusion Controlled Systems: Hydrogels", *Polymers for Controlled Drug Delivery*, CRC Press, Inc., 1991, Ch. 2, pp. 16–37.

Thompson et al., "Heparin and Growth Control of Vascular Cells," *Ann. N.Y. Acad. Sci.* 556:255–267 (1989).

Tidd et al., "Comparison of Hydrophilic Polymer–Coated Latex, uncoated Latex and PVC Indwelling Balloon Catheters in the Prevention of Urinary Infection," *J.Urol.* 48:285–291 (1976).

Tokuhiro et al., "NMR Study of Poly(N–isopropylaacrylamide) Gels near Phase Transition", 1991, *Macromolecules*, 24:2936–43.

Waller B.F. et al., "Vessel Wall Pathology After Angioplasty", CARDIO, Aug. 1990, pp. 57, 70–72, 81.

Waller et al., "Morphologic Observations Late after Coronary Balloon Angioplasty" Mechanisms of Acute Injury and Relationship to Restenosis, *Radio.* 174:961–967 (Mar. 1990).

Wolinsky H. et al., "Local Introduction of Drugs into the Arterial Wall: A Percutaneous Catheter Technique", Journal of Interventional Cardiology, vol. 2, No. 4, 1989, pp. 219–228.

The Andreas Gruentzig Cardiovascular Center News Letter (Spring 1990).

Supplementary European Search Report, EP 92 90 3283, mailed Sep. 15, 1993.

International Search Report for PCT/US91/09804, mailed 08 Apr. 1992.

International Search Report, PCT/US91/09805, mailed 8 Apr. 1992.

International Search Report, PCT/US94/08394, mailed 23 Dec. 1994.

Slepian, "Polymeric Endoluminal Gel Paving: Therapeutic Hydrogel Barriers and Sustained Drug Delivery Depots for Local Arterial Wall Biomanipulation", *Semin Intervent Cardiol*, 1:103–116 (1996).

Szikora et al., "Endovascular Treatment of Experimental Aneurysms with Lipid Polymers: The Protective Potential of Stents", *Neurosurgery*, 38(2):339–47 (1996).

Wakhloo et al., "Self–Expanding and Balloon–Expandable Stents in the Treatment of Cartoid Aneurysms: An Experimental Study in a Canine Model", Am. J. *Neuroradiology*, 15:494–502 (1994).

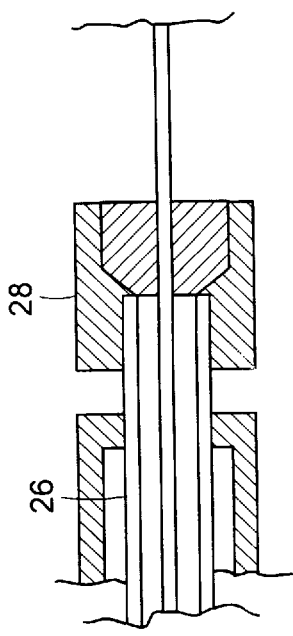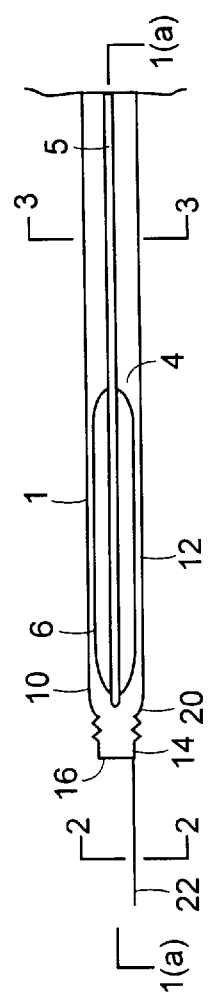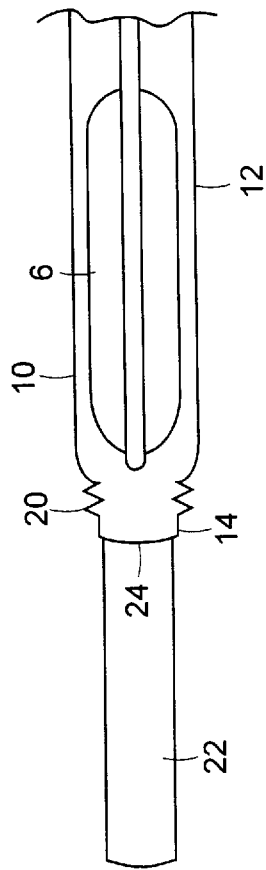

DRUG DELIVERY BALLOON CATHETER DEVICE

This application relates to delivering drugs internally to a patient's body.

BACKGROUND OF THE INVENTION

Balloon catheters may be used to deliver drugs to tissue at a desired location of a body lumen or cavity. Typically, the balloon is positioned at the desired location for drug delivery by sliding it through portions of the body lumen or cavity where no drug delivery is desired. Consequently, it may be difficult to avoid undesired drug release during the positioning of the balloon, particularly when the body lumen or cavity transports bodily fluids into which the drug may be released.

U.S. Pat. No. 5,304,121 describes a drug delivery system that uses a hydrogel coating. The '121 patent discloses a rigid sheath member extendable over the hydrogel coating to help prevent the release of the drug into bodily fluids. The entire disclosure of the '121 patent is hereby incorporated herein by reference.

SUMMARY OF THE INVENTION

One aspect of the invention generally features a medical device for delivering a drug internally to a patient's body. The device includes a catheter with a catheter shaft and a balloon attached to a distal end of the catheter shaft and a flexible, thin-walled sheath extending over the balloon. The sheath helps to prevent the premature release of the drug during the positioning of the balloon at the desired location for drug delivery. Because the sheath is flexible and thin-walled, the flexibility and outer diameter of the catheter are only minimally affected by the addition of the sheath.

The sheath includes a balloon-enveloping portion having an inner diameter sized to fit closely around the balloon and a collar distal to, and having an inner diameter slightly smaller than the inner diameter of, the balloon-enveloping portion. The collar terminates in an opening. The collar has a slightly smaller inner diameter to help prevent the balloon from sliding out of the opening during the positioning of the balloon at the desired location for drug delivery.

To facilitate the use of a flexible, thin-walled sheath which might otherwise be difficult to manipulate in certain operations described below in which the relative positions of the sheath and balloon are adjusted, a tab extends distally from the wall of the sheath. The tab also may be a continuation of part of the wall of the sheath. The tab is used to adjust the sheath with respect to the catheter. Because the tab should be removed before the device is inserted into the patient's body, the sheath may have pre-formed cuts located where the tab is attached to the sheath. The tab is detachable from the sheath by tearing the sheath along the pre-formed cuts.

The sheath also may have indentations located at the balloon-enveloping portion to engage the balloon. The indentations are transverse to the balloon axis and help to prevent the balloon from sliding out of the opening during the positioning of the balloon at the desired location for drug delivery.

The wall of the sheath has a thickness of no more than 0.04 French. Also, the sheath may be made from polyester, nylon or polyethylene terephthalate (PET).

In another aspect, the invention generally features a device in which the balloon is coated with a hydrogel polymer matrix having a drug embedded therein.

In yet another aspect, the invention generally features a method for delivering a drug internally to a patient's body by providing the above-described device; uncovering the balloon by pushing the balloon out of the opening of the sheath; preparing the balloon by introducing the drug to the surface of the balloon; and covering the balloon by pulling the balloon back through the opening of the sheath until the balloon is proximal of the sheath opening. The method also may include steps such as inserting the device into the body to position the balloon at a desired location of drug delivery; delivering the drug to the body; and removing the device from the body.

Moreover, the outer surface of the balloon may be covered with a hydrogel coating before the uncovering step, and the preparing step may comprise introducing the drug to the hydrogel coating. In another embodiment, the outer surface of the balloon may be covered with both a hydrogel coating and the drug during the preparing step. The balloon also may be expanded within the sheath to form a seal between the outer surface of the balloon and the inner surface of the sheath. This helps to prevents bodily fluids from flowing into the sheath.

If the sheath has a tab, the method may include the steps of covering the balloon by holding the tab and pulling the balloon back through the opening of the sheath until the balloon is proximal of the sheath opening and detaching the tab from the sheath. The detaching step may include tearing the sheath along the pre-formed cuts located where the tab is attached to the sheath.

Other features and advantages will be apparent from the following drawings, description of the preferred embodiments and claims.

BRIEF DESCRIPTION OF THE DRAWING

FIG. 1 is a side view, partially in section, of a device for delivering a drug internally to a patient's body.

FIG. 1(a) is a cross-sectional view along lines 1(a)–1(a) in FIG. 1.

DESCRIPTION OF THE PREFERRED EMBODIMENTS

Figure 2:
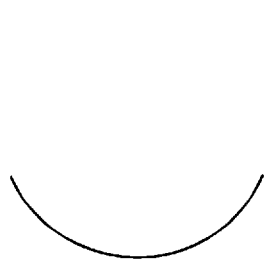
FIG. 2 is a cross-sectional view along lines 2—2 in FIG. 1.
Figure 3:
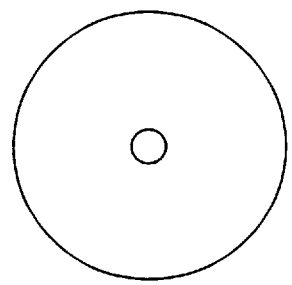
FIG. 3 is a cross-sectional view along lines 3—3 in FIG. 1.

Referring to FIGS. 1–3, a drug delivery balloon catheter device 1 includes a catheter 4 with a catheter shaft 5 and an expandable balloon 6 attached to a distal end of catheter shaft 5. Device 1 also includes a flexible, thin-walled sheath 10 extending over balloon 6. Sheath 10 helps to prevent the premature release of the drug during the positioning of balloon 6 at the desired location for drug delivery, for example, when sliding balloon 6 through a blood vessel.

Catheter shaft 5 is preferably very small in diameter and flexible. Catheter shaft 5 may be formed of hollow tubing to which balloon 6 is attached. Balloon 6 is preferably made from a compliant material such as polyethylene which conforms to the shape of the body lumen wall. Balloon 6 may also be made from other materials used in angioplasty, e.g., a nondistending material, such as polyethylene terephthalate (PET).

Balloon 6 has a swellable hydrogel polymer coating which can absorb a substantial amount of the drug, typically in aqueous solution form. The hydrogel polymer coating is swellable and, in use, the hydrogel releases the drug. The hydrogel may itself be released from the surface of the balloon, or it may release the drug while generally remaining adhered to the balloon (see the '121 patent). Those of ordinary skill in the art will understand that there are a number of suitable hydrogel polymers that can be used, such as cross-linked polymer materials formed from the combination of a colloid and water.

The drug is preferably water soluble so that it may be easily absorbed into the hydrogel polymer coating. The hydrogel polymer and drug preferably are not complexed, i.e., they are held together primarily if not exclusively through non-covalent association that results when the hydrogel polymer swells and absorbs the drug. In other embodiments, however, it may be advantageous to select a hydrogel polymer coating for a particular drug such that the drug is not substantially released into bodily fluids before expanding balloon 6. Binding of the drug may be accomplished by electrostatic attraction of the drug to the coating or a coating additive or by mechanical binding, e.g., using a coating having a pore size that inhibits inward flow of bodily fluids or outward flow of the drug.

The drug may be an antithrombogenic drug or an antiproliferative drug. Antithrombogenic drugs include heparin, PPack (dextrophenylalanine proline arginine chloromethylketone), enoxaprin, aspirin and hirudin. Antiproliferative drugs include monoclonal antibodies capable of blocking smooth muscle cell proliferation, heparin, angiopeptin and exoxaprin.

The dosage applied to the tissue may be controlled by regulating the time of presoaking the drug into the hydrogel polymer coating to determine the amount of absorption of the drug solution by the hydrogel polymer coating. Other factors affecting the dosage are the concentration of the drug in the solution applied to the coating and the releasability of the hydrogel polymer coating determined by, for example, the thickness of the hydrogel polymer coating, its resiliency, porosity and the ability of the hydrogel polymer coating to retain the drug.

To protect against premature release of the drug and hydrogel, catheter 4 is covered by sheath 10 during the positioning of balloon 6 at the desired location for drug delivery. Sheath 10 is flexible and has a thickness of no more than 0.04 French. Thus, sheath 10 increases the outer diameter of catheter 4 by only approximately 0.1 French. Although sheath 10 is preferably made from polyethylene terephthalate (PET), sheath 10 also may be made from nylon or polyester. Thus, the flexibility and outer diameter of catheter 4 are only minimally affected by the addition of sheath 10.

Sheath 10 has a balloon-enveloping portion 12 and a collar 14. Balloon-enveloping portion 12 has an inner diameter sized to fit closely around folded balloon 6. Collar 14 is distal to, and has an inner diameter slightly smaller than the inner diameter of, the balloon-enveloping portion 12. Collar 14 terminates in an opening 16. The slightly smaller inner diameter of collar 14 helps to prevent balloon 6 from sliding out of opening 16 during the positioning of balloon 6 at the desired location for drug delivery.

Sheath 10 also has indentations 20 in the wall of sheath 10 located at a distal end of balloon-enveloping portion 12. Indentations 20 help to prevent balloon 6 from sliding out of opening 16 during the positioning of balloon 6 at the desired location for drug delivery. Indentations 20 are molded into the wall of sheath 10 and are transverse to the balloon axis. Indentations 20 may be straightened out temporarily by pulling on the wall of sheath 10.

Sheath 10 also includes a tab 22 extending distally from the wall of sheath 10. Tab 22 may be used to adjust sheath 10 with respect to catheter 4. As described below, tab 22 should be removed from sheath 10 before insertion into the patient's body. Removal is achieved by tearing along preformed cuts 24 in the wall of sheath 10, located where tab 22 is attached to sheath 10.

Finally, device 1 may include a relatively stiff tubing 26 and adapter 28 disposed at the proximal end (outside the patient's body) for a better seal between sheath 10 and catheter 4. II. Use Referring to FIGS. 4–9, a drug may be delivered internally to the patient's body using device 1 as follows.

Figure 4:
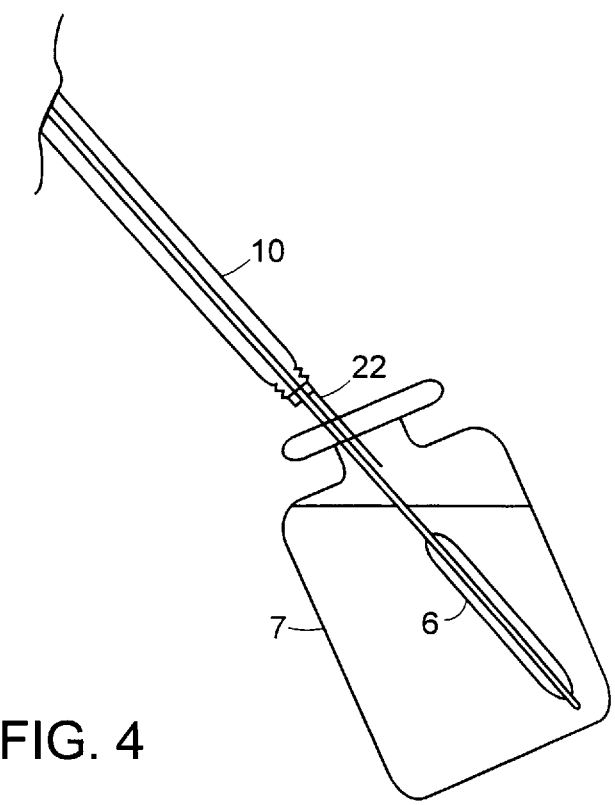
FIGS. 4–9 show the steps of delivering a drug internally to the patient's body using the device in FIG. 1.

Drug and hydrogel coating typically are added to the balloon surface shortly before the device is inserted into the patient's body. First, balloon 6 is exposed by pushing it out of opening 16 of sheath 10. Balloon 6 is expanded, and a drug in an aqueous solution is absorbed into the hydrogel polymer coating, for example by immersing it in a small vial 7 containing the drug, as shown in FIG. 4. Alternatively, the drug may be applied to the balloon in the form of droplets from an eyedropper, or it may be precipitated into the hydrogel polymer coating before sterilization and the coated balloon catheter is sold as a finished device.

Figure 5:
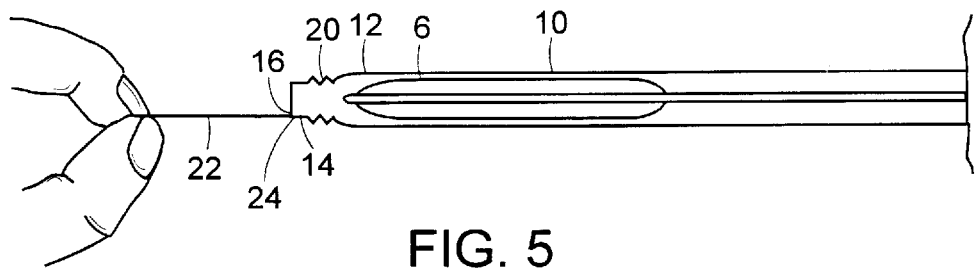
Figure 6:
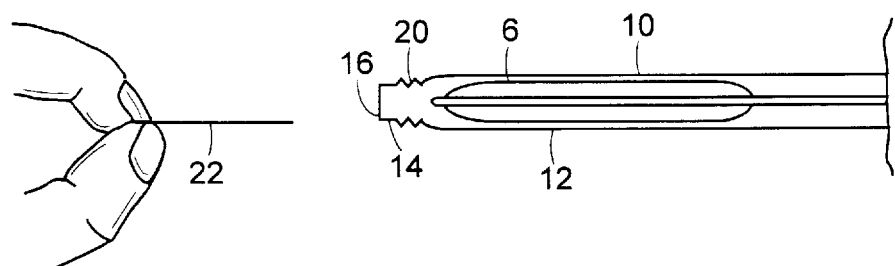

After balloon 6 is dried and deflated, balloon 6 is covered with sheath 10 by pulling balloon 6 back into sheath 10 while holding tab 22, as shown in FIG. 5. Balloon 6 is positioned within sheath 10, so that balloon 6 is proximal of collar 14 of sheath 10. Tab 22 is detached from sheath 10 by tearing or cutting along pre-formed cuts 24 (FIG. 6) before inserting the device into the patient.

Although tab 22 is helpful in manipulating the flexible, thin-walled sheath, other embodiments of the invention may describe other ways for adjusting the relative positions of the sheath and balloon. For example, the balloon may be pulled back into the sheath by using forceps to hold the sheath. In another embodiment, the balloon may be covered with the sheath by unrolling the sheath over the balloon.

After balloon 6 is positioned within sheath 10, balloon may be slightly expanded so that the outer surface of balloon 6 contacts with the inner surface of sheath 10, thereby forming a seal between the outer surface of balloon 6 with the inner surface of sheath 10. This helps to prevent bodily fluids from flowing into sheath 10. Balloon 6 is then deflated.

Figure 7:
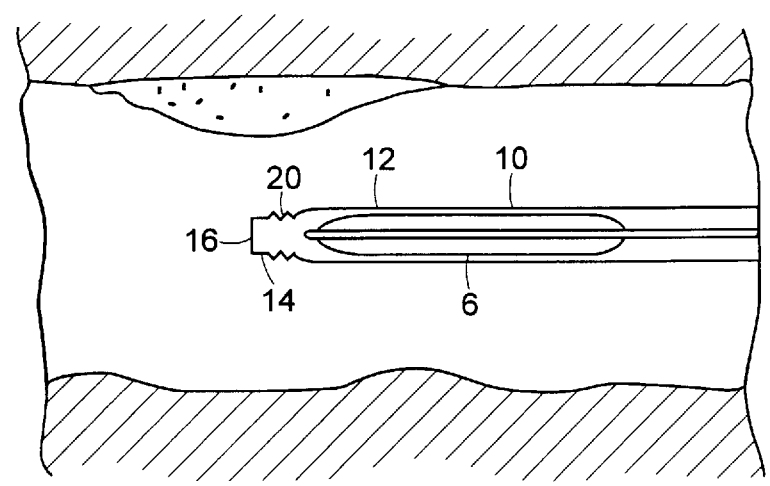

In FIG. 7, device 1 is inserted into a blood vessel having a region to be treated, such as an occlusion due to deposits of plaque on the vessel wall tissue. Device 1 is moved along the vessel to position balloon 6 at the desired location for drug delivery.

Figure 8:
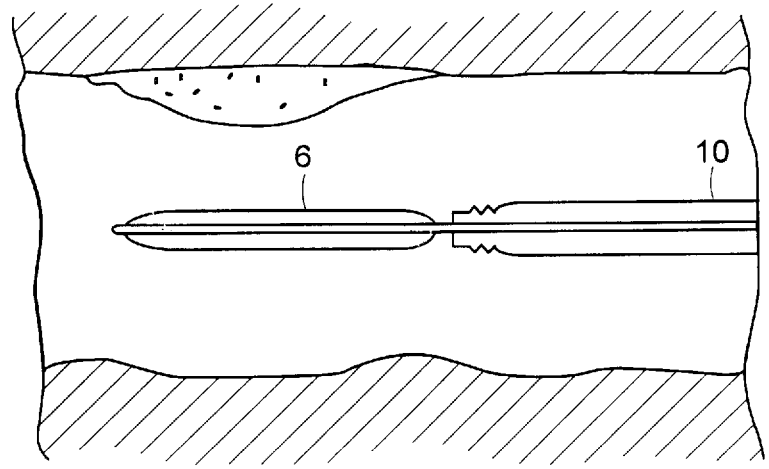
Figure 9:
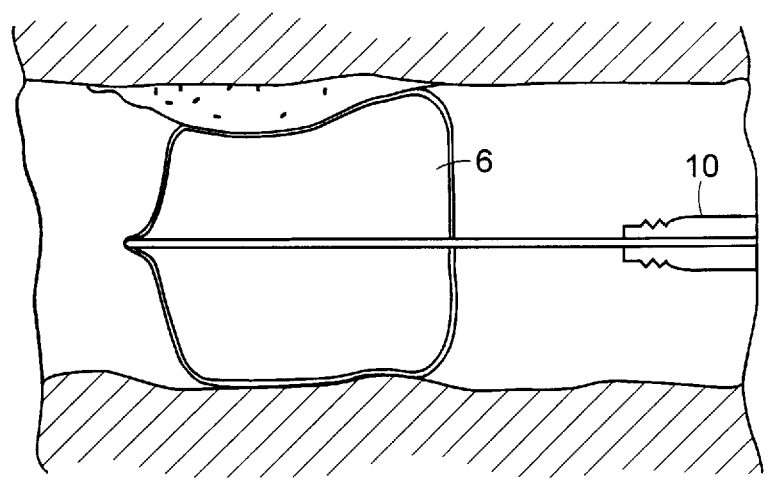

Referring to FIG. 8, after balloon 6 is positioned at desired location for drug delivery, balloon 6 is uncovered by pulling on sheath 10 while maintaining balloon 6 in position. Balloon 6 slides out of opening 16 of sheath 10. As balloon 6 is expanded, the drug is released for transfer into the plaque and tissue. As shown in FIG. 9, the pressure applied to the plaque and tissue by the expansion of balloon 6 enhances the transfer of the drug into the plaque and tissue. After the drug is delivered to the tissue, balloon 6 is deflated and removed from the patient's body.

What is claimed is:

1. A medical device for delivering a drug internally to a patient's body comprising:

a catheter with a catheter shaft and a balloon attached to a distal end of the catheter shaft; and a flexible, thin-walled sheath extending over the balloon, wherein the sheath includes
  a balloon-enveloping portion having an inner diameter sized to fit closely around the balloon, and
  a collar distal to, and having an inner diameter slightly smaller than the inner diameter of, the balloon-enveloping portion, the collar terminating in an opening.

2. The device of claim 1 further comprising a tab extending distally from the wall of the sheath.

3. The device of claim 2 wherein the tab is a continuation of part of the wall of the sheath.

4. The device of claim 2 wherein the sheath has pre-formed cuts located where the tab is attached to the sheath.

5. The device of claim 4 wherein the tab is detachable from the sheath by tearing the sheath along the pre-formed cuts.

6. The device of claim 1 wherein the sheath has indentations located at the balloon-enveloping portion to engage the balloon.

7. The device of claim 1 wherein the wall of the sheath has a thickness of no more than 0.04 French.

8. The device of claim 1 wherein the sheath is made from polyester, nylon or polyethylene terephthalate (PET).

9. The device of claim 1 wherein the balloon is coated with a hydrogel polymer matrix having a drug embedded therein.

10. A method for delivering a drug internally to a patient's body comprising:
  providing the device of claim 1;
  uncovering the balloon by pushing the balloon out of the opening of the sheath;
  preparing the balloon by introducing the drug to the surface of the balloon; and
  covering the balloon by pulling the balloon back through the opening of the sheath until the balloon is proximal of the sheath opening.

11. The method of claim 10 further comprising:
  inserting the device into the body to position the balloon at a desired location of drug delivery;
  delivering the drug to the body; and
  removing the device from the body.

12. The method of claim 10 wherein the outer surface of the balloon is covered with a hydrogel coating before the uncovering step, and the preparing step comprises introducing the drug to the hydrogel coating.

13. The method of claim 10 wherein the outer surface of the balloon is covered with both a hydrogel coating and the drug during the preparing step.

14. The method of claim 10 further comprising expanding the balloon within the sheath to form a seal between the outer surface of the balloon and the inner surface of the sheath.

15. A method for delivering a drug internally to a patient's body comprising:
  providing the device of claim 2;
  uncovering the balloon by pushing the balloon out of the opening of the sheath;
  preparing the balloon by introducing a drug to the surface of the balloon;
  covering the balloon by holding the tab and pulling the balloon back through the opening of the sheath until the balloon is proximal of the sheath opening; and
  detaching the tab from the sheath.

16. The method of claim 14 wherein the detaching step comprises tearing the sheath along pre-formed cuts located where the tab is attached to the sheath.

* * * * *